United States Patent [19]

Nunokawa

[11] Patent Number: 4,468,104
[45] Date of Patent: Aug. 28, 1984

[54] WORKING DISTANCE DETECTING DEVICE FOR OPHTHALMIC INSTRUMENTS

[75] Inventor: Kazuo Nunokawa, Tokyo, Japan

[73] Assignee: Tokyo Kogaku Kikai Kabushiki Kaisha, Japan

[21] Appl. No.: 289,070

[22] Filed: Jul. 31, 1981

[30] Foreign Application Priority Data

Aug. 4, 1980 [JP] Japan ................... 55-106925

[51] Int. Cl.³ ............................................. A61B 3/14
[52] U.S. Cl. ..................................... 351/206; 351/208
[58] Field of Search ................... 351/206, 207, 208; 356/399

[56] References Cited

U.S. PATENT DOCUMENTS 4,253,743  3/1981  Matsumura ................... 351/208

Primary Examiner—John K. Corbin
Assistant Examiner—P. M. Dzierzynski
Attorney, Agent, or Firm—Brumbaugh, Graves, Donohue & Raymond

[57] ABSTRACT

A working distance detecting device for ophthalmic instruments has two annular slits in the illuminating system. One of the annular slits has a light-shading portion of a predetermined width. A light-receiving portion is provided around the object lens so as to receive beams of light reflected at the cornea of the eye to be examined. The working distance can be detected at the light-receiving portion by the image of the light-shading portion of the annular slit.

5 Claims, 8 Drawing Figures

WORKING DISTANCE DETECTING DEVICE FOR OPHTHALMIC INSTRUMENTS

BACKGROUND OF THE INVENTION

The present invention relates to a working distance detecting device in an ophthalmic apparatus.

In an ophthalmic apparatus such as a funduscopic camera, illuminating beams are projected on an eye to be examined through an object lens located at a position confronting the eye to be examined, and in case of a funduscopic camera, an arrangement is made such that reflected beams of the projected light from the fundus are guided to a photographic optical system. In not only such funduscopic camera but also other ophthalmic apparatus in which illuminating beams are projected on an eye to be examined through an object lens and a flux of beams reflected from the interior of the eye to be examined is guided to a photographic optical system or an observation optical system, there is a risk of occurrence of a flare or ghost because of intrusion of illuminating beams reflected from the face of the cornea of the eye into the photographic or observation optical system.

As means for overcoming this problem of occurrence of a flare or ghost by a flux of reflected beams of illuminating light, there has heretofore been adopted an arrangement in which an annular slit is formed in an illuminating optical system, an apertured mirror is slantingly disposed along the optical axis of the object lens at a position substantially conjugate to the pupil of an eye to be examined with respect to the object lens, an annular flux of illuminating beams passing through the annular slit is once focussed on an annular reflection surface of the perforated mirror and the flux is then made incident into the eyeball through the pupil of the eye from the object lens. If this arrangement is adopted, occurrence of a flare or ghost due to reflection of illuminating beams on the cornea can be prevented when the perforated mirror is located at a position substantially conjugate to the pupil of the eye with respect to the object lens. More specifically, since the distance between the object lens and the perforated mirror is always constant, when the distance between the object lens and the eye, that is, the working distance, is appropriate, occurrence of a flare or ghost can be prevented.

Accordingly, in an ophthalmic apparatus of this type, it is very important to maintain an appropriate working distance while the apparatus is used. This appropriate working distance has heretofore been obtained by delicately moving the apparatus by an operator while observing a picture image produced in an observation optical system, that is, a picture image produced on a Braun tube of a monitor television when illuminating beams are infrared rays or a picture image seen through an eye when illuminating beams are visible rays. When this conventional method is adopted, since not only this operation of adjusting the working distance but also other complicated operations such as the operation of adjustment of alignment of the optical axis of the object lens with the eye to be examined and the focussing operation should simultaneously be performed, a minute flare or ghost is apt to be overlooked. Furthermore, in an ophthalmic apparatus of the type where the operation of alignment adjustment and the focussing operation are carried out by using infrared rays, it is very difficult to detect rays diffused on the cornea or the crystalline lens on a Braun tube of a television.

As means for eliminating this disadvantage, a proposal has been made by Japanese Pat. application No. 81631/79. According to this proposal, a light-receiving portion is disposed in the peripheral region of an object lens and the working distance between the object lens and the face of the cornea of an eye to be examined is detected according to the position of the flux of beams reflected from the cornea on this light-receiving portion. The light receiving portion may be constructed, for example, by a light-receiving plate arranged coaxially with the object lens in the peripheral region of the object lens. In this case, when the radius of the inner circumference of an image of illuminating beams reflected from the cornea, which is formed on the surface of the light-receiving plate, has a predetermined value, it is judged that the working distance is appropriate. Furthermore, the state of alignment of the object lens with an eye to be examined can be known by examining whether or not the inner circumference of the image formed on the surface of the light-receiving plate is coaxial with the optical axis of the object lens.

This working distance detecting device is very advantageous over the conventional ones because the working distance and alignment can be detected very conveniently. Furthermore, if an optical fiber or photoelectric element is used instead of the light-receiving plate, necessary display can easily be accomplished on an image forming portion of the observation optical system. However, in this device, since both the working distance and alignment are detected only by detecting the position of the inner circumference of the annular slit image formed by beams reflected from the cornea of the eye being examined, actual adjustment involves some problems or difficulties. Furthermore, for example, when the field angle of the object lens is larger than 45°, occurrence of a flare or ghost due to overlapped passage of the flux of illuminating beams and the flux of beams reflected from the fundus on the front face of the crystalline lens and the cornea is prevented by arranging annular slits at conjugate positions on the front face and the cornea, respectively. In this case, the flux of illuminating beams in the vicinity of the front face of the crystalline lens conjugate to the light-receiving surface with respect to the cornea has a cylindrical shape in which changes of the diameters of the inner and outer circumferences are small. Accordingly, the change of the radius of the inner circumference on the surface detecting the flux of illuminating beams reflected from the cornea is small as compared with the change of the operation distance, and therefore, precise measurement of the operation distance is practically very difficult.

SUMMARY OF THE INVENTION

It is a primary object of the present invention to provide a working distance detecting device utilizing an annular slit image formed by beams reflected from the cornea of an eye to be examined in a funduscopic camera comprising two annular slits, in which an information different from the information used for detecting the alignment state is used for detecting the working distance.

According to the present invention, the above and other objects can be accomplished by an ophthalmic instrument comprising a first annular slit adapted to be located at a position substantially conjugate to a cornea of an eye to be examined with respect to an object lens confronting the eye to be examined and a second annular slit disposed with a predetermined distance from said first annular slit, means for projecting a flux of illuminating beams on the eye through said slits and the object lens, a working distance detecting device which comprises at least one light-shading portion provided in one of said annular slits and having a width in a circumferential direction, and a light-receiving portion provided around said object lens at a position corresponding to said light-shading portion of an image of said annular slit formed by beams of the illuminating beam flux reflected from the cornea of the eye, whereby the working distance between the object lens and the face of the cornea of the eye is detected based on the width of the light-shading portion of the annular slit image at said light-receiving portion.

BRIEF DESCRIPTION OF THE DRAWING

In order that the invention be more clearly understood, descriptions will now be made with respect to a preferred embodiment taking reference to the accompanying drawing, in which.

DESCRIPTION OF PREFERRED EMBODIMENTS

Figure 1:
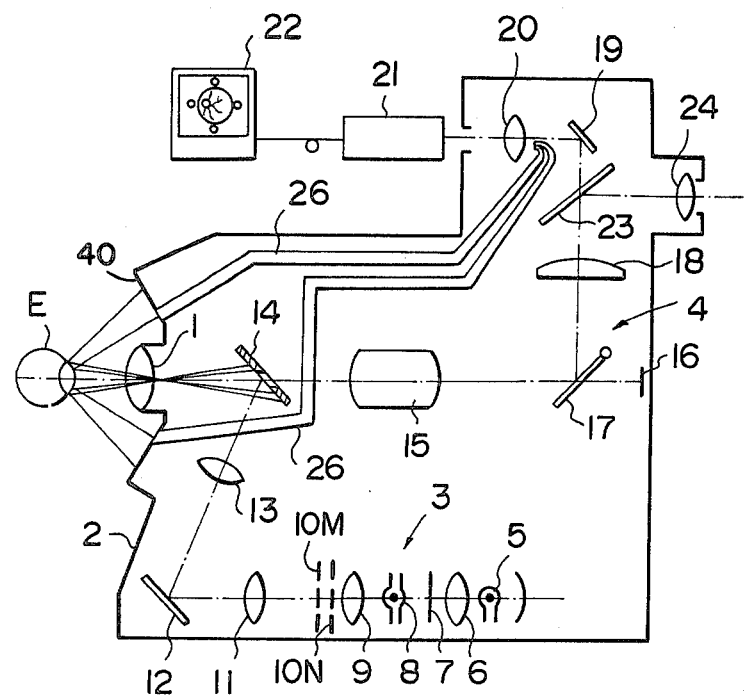
FIG. 1 is a diagrammatical view of a funduscopic camera in accordance with one embodiment of the present invention.

Referring now to the drawing, particularly to FIG. 1, there is shown a funduscopic camera which comprises an object lens 1 adapted to be located so as to confront an eye E to be examined, an illuminating optical system 3, and an observation or photographic optical system 4 which are contained in a housing 2. The illuminating optical system 3 comprises an illuminating light source 5 for observation and a photographic light source 8, such as a xenon tube, which is arranged to confront the light source 5 through a condenser lens 6 and a red filter 7. Beams from these light sources are converged by a condenser lens 9 and are focussed in the form of an annular image on the reflection face of an apertured mirror 14 slantingly disposed on the optical axis of the object lens 1, through a relay lens 11, a reflecting mirror 12 and a relay lens 13 from an annular slit 10M and a C-shaped slit 10N. The beams are reflected from the reflecting face of the mirror 14 toward the object lens 1 and projected on the eye E to be examined through the object lens 1.

The beam reflected from the fundus of the eye E are made incident on the funduscopic camera from the object lens 1 and pass through the central aperture of the mirror 14 to be made incident on the observation or photographic optical system 4. The observation optical system 4 has a focussing lens 15 and beams which have passed through this lens 15 are focussed in the form of an image on the surface of a photographic film 16. A mirror 17 is slantingly disposed in front of the surface of the photographic film 16 so that the mirror 17 is retracted in the photographing operation. The beams reflected from the mirror 17 are focussed on the imaging plane of a field lens 18, and the beams passing through the field lens 18 are reflected by a reflecting mirror 19 and focussed on the photoelectric surface of a taking tube 21 through a focussing lens 20. Signals from the taking tube 21 are transmitted to a monitor television 22 to form a picture image on the screen of a Braun tube. Another mirror 23 is slantingly disposed between the field lens 18 and mirror 19, and the beams reflected from this mirror 23 are observed through an eye lens 24. The mirror 23 may be disposed so that is optionally retreated from an observation optical path.

The illuminating light beams projected through the object lens 1 to the eye E are partially reflected at the cornea of the eye E toward a light-receiving surface 40 provided around the object lens 1 to form an image of the annular slits.

Figure 2:
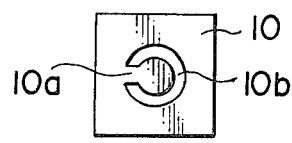
FIG. 2 is a front view showing one embodiment of the annular slit aperture.
Figure 3:
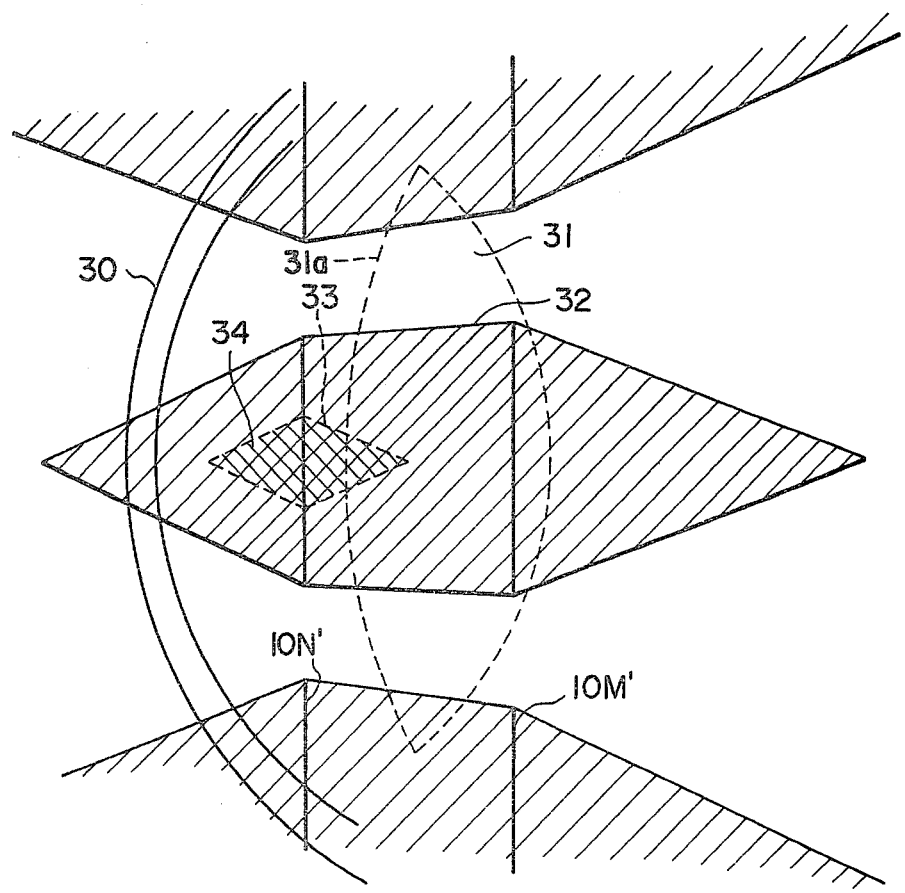
FIG. 3 is a view showing the light path in the eye to be examined.
Figure 4A:
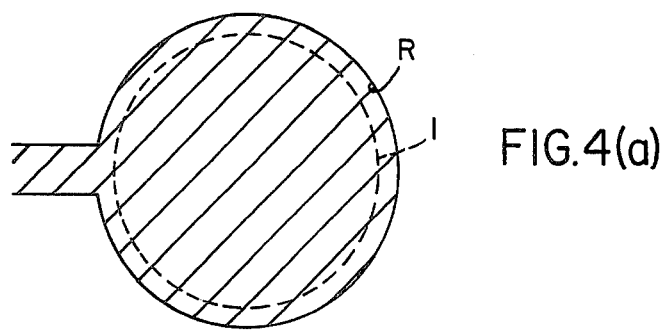
FIGS. 4A, 4B, and 4C show the positional relationship between the object lens and the image of the annular slit formed by beams of light reflected at the cornea of the eye.
Figure 4B:
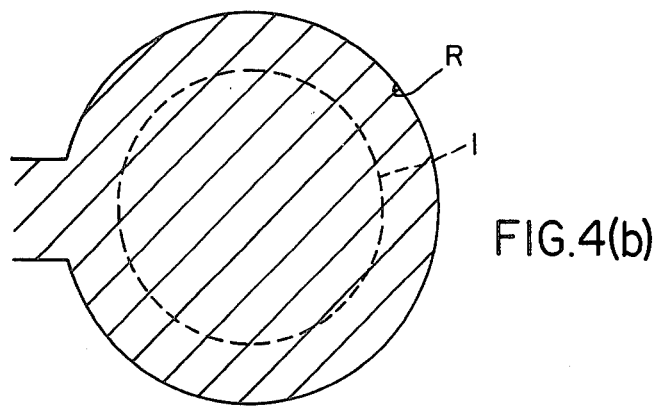
Figure 4C:
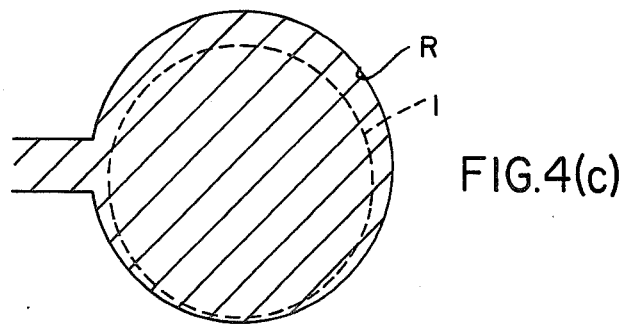
Figure 5:
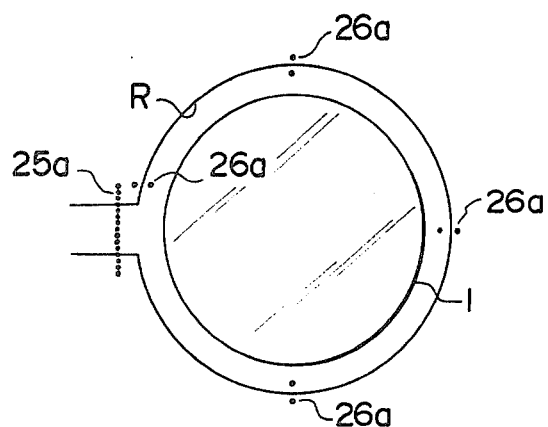
FIG. 5 shows an example of the light-receiving portion.

The annular slit 10M has a completely ring-like shape, and the annular slit 10N has not a completely ring-like shape but consists of a substantially C-shaped transmitting portion 10b including a light-shading portion 10a having a certain width in the circumferential direction, as shown in FIG. 2. Referring to FIG. 3, it will be noted that an image of the annular slit 10M is formed in the eye at the location 10M' and an image of the C-shaped slit 10N is formed in the eye at the location 10N'. The shaded areas in FIG. 3 designate the regions through which the beams illuminating the fundus do not pass. In the vicinity of the front face 31a of the crystalline lens 31 which is conjugate to the light-receiving face with respect to the cornea 30, the portion 32 through which the flux of illuminating beams does not pass has a substantially cylindrical shape as shown by shadows. Accordingly, even if there is a change in the working distance, the portion on the light-receiving face 31a corresponding to the inner circumference 32 of the illuminating beam flux is not substantially shifted so that it is difficult to detect a change of the working distance. Referring to the illuminating beam flux at a section along a plane parallel to the optical axis and passing through the center of the image of the light-shading portion 10a of the C-shaped slit 10N, i.e. a plane perpendicular to the plane of FIG. 3, the portion through which the beam flux does not pass is designated by a rhombic portion 34 surrounded by lines 33 which is disposed behind the plane of FIG. 3. When the working distance is changed, since the of the boundary 33 of the beam flux on the light-receiving face 31a produced by the light-shading portion 10a of the C-shaped slit 10N is much larger than the of the above-mentioned circumference 32 of the illuminating beam flux, the precision of detection of the working distance is ensured. A part of the flux of beams projected on the eye E to be examined through the object lens 1 is relfected on the face of the cornea of the eye to form an annular slit image in the peripheral region of the object lens 1. This annular slit image as represented by symbol R in FIG. 4-A is coaxial with the object lens 1 when an appropriate working distance is maintained between the object lens 1 and the eye E and also an appropriate alignment is kept, and in this case, the radius of the inner circumference of the annular slit image has a predetermined value and the width of the portion corresponding to the light-shading portion 10 has a predetermined value. In contrast, when the working distance is too short, as shown in FIG. 4-B, the radius of the inner circumference of the annular slit image R is substantially the same as the predetermined value but the width of the portion corresponding to the light-shading portion 10a is larger than the predetermined value. If the alignment is not appropriate, as shown in FIG. 4-C, the annular slit image R is not coaxial with the object lens 1.

For detecting such changes of images of the annular slit and C-shaped slit, ends 25a and 26a of optical fibers 25 and 26, each constituting a light-receiving portion, are arranged. A first light-receiving portion consists of ends 25a of optical fibers 25 arranged at a position confronting the light-shading portion 10b in rows traversing the image of the light-receiving portion 10a in the direction of the width, and a second light-receiving portion consists of ends 26a of a plurality of pairs of adjoining optical fibers 26 which are arranged on the same circular lines, so that when the working distance and the alignment are appropriate, the inner circumference of the annular slit image R is interposed between each paired optical fibers 26a. The angle between every two adjoining pairs of the optical fibers 26 is 90°. The other ends 25b and 26b of the optical fibers 25 and 26 are arranged on the front side of the image forming lens 20 so that beams passing through these ends 25b and 26b are imaged on the monitor television 22 by the taking tube 21.

Figure 6:
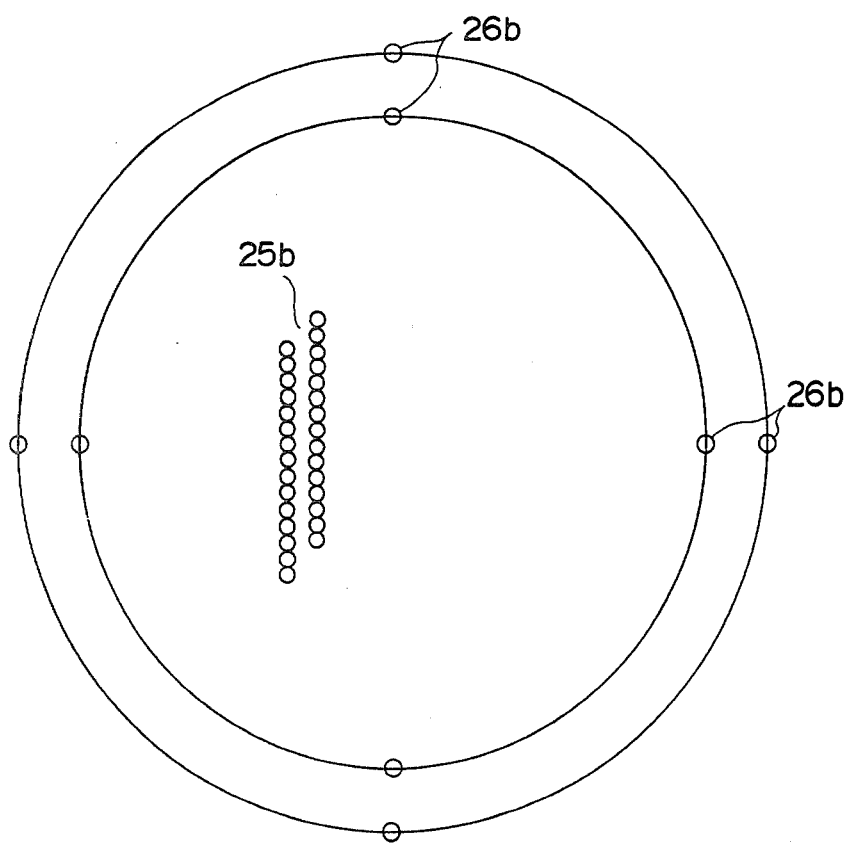
FIG. 6 shows an example of the arrangement at the observing section.

In connection with the arrangement of the fiber ends 25b, for example, a row of fiber ends 25b corresponding to the fiber ends 25a are divided into two segments and appropriate numbers of corresponding fiber ends 25b of the respective segments are overlapped to each other, as shown in FIG. 6. The so arranged fiber ends 25b are observed on the monitor television, and if bright-dark boundaries are made in agreement in the two segments of the fiber ends 25b, an appropriate working distance can be obtained. In this case, an improper alignment results only in a vertical movement of the boundaries, and detection of the working distance is not influenced by this improper alignment. It is preferred that the fiber ends 25b be arranged as described above. Of course, however, other arrangements may optionally be adopted. The paired fiber ends 26b may be arranged on the same circles so that the angular interval between every two adjacent pairs of the fiber ends 26b is 90°, as shown in FIG. 6. These four pairs of fiber ends 26b are observed on the monitor television, and adjustment is made so that the inner fiber ends 26b are seen dark and the outer fiber ends 26b are seen bright. Of course, photoelectric elements and the like may be used as the detecting means instead of such optical fibers.

According to the present invention, the working distance between the object lens and the eye to be examined is detected by the width of the image of the light-shading portion of the annular slit, which is reflected from the face of the cornea of the eye, and if necessary, the alignment is judged according to the positional relationship between the inner circumference of the image of the annular slit and the object lens. Therefore, the operations can be performed very conveniently and occurrence of an erroneous operation can be prevented completely.

The invention has thus been shown and described with reference to a specific embodiment, however, it should be noted that the invention is in no way limited to the details of the illustrated arrangements but changes and modifications may be made without departing from the scope of the appended claims.

I claim:

1. An ophthalmic instrument comprising an observing optical system for observing a patient's eye, said observing optical system having objective lens means adapted to be located at a working distance from the cornea of a patient's eye, an illuminating optical system having an illuminating optical axis for projecting beams of illuminating light to the patient's eye through the objective lens means, said illuminating optical system including a first annular aperture adapted to be located at a position substantially conjugate with the cornea of the patient's eye with respect to the objective lens means, a second annular aperture spaced by a predetermined distance along said illuminating optical axis from said first annular aperture, at least one light-shading portion provided in one of said annular apertures and having a selected width in the circumferential direction, light source means for projecting the beams of illuminating light to the eye through said apertures and the objective lens means, and a working distance detecting device comprising a light-receiving portion disposed around said objective lens means at a position corresponding to said light-shading portion of an image of said one annular aperture formed by beams of the illuminating light reflected from the cornea of the eye, whereby the working distance between the objective lens means and the cornea of the eye is detected based on the width of the light-shading portion of the image of said one annular aperture at said light-receiving portion.

2. An ophthalmic instrument in accordance with claim 1 in which said light-receiving portion includes one set of ends of optical fibers which are arranged at a portion where the image of the light-shading portion is to be produced, the other set of ends of the optical fibers being positioned at an observing section of the instrument.

3. An ophthalmic instrument in accordance with claim 2, in which said one set of ends of the optical fibers are arranged in a row widthwisely crossing said image of the light-shading portion.

4. An ophthalmic instrument in accordance with claim 2 in which said other set of ends of the optical fibers are arranged in two rows so that boundaries of dark-bright ends are aligned between the rows when a correct working distance is established.

5. An ophthalmic instrument in accordance with claim 1 in which a plurality of pairs of optical fibers are arranged so that the image of said one annular aperture has an inner circumference interposed between ends of each pair of optical fibers when correct working distance and alignment are established.

* * * * *